United States Patent [19]

Chao et al.

[11] 4,166,135

[45] Aug. 28, 1979

[54] METHOD FOR MODIFYING THE FLAVOR OF YEAST

[75] Inventors: Kwei C. Chao, Naperville, Ill.; John A. Ridgway, LaPorte, Ind.

[73] Assignee: Standard Oil Company (Indiana), Chicago, Ill.

[21] Appl. No.: 826,858

[22] Filed: Aug. 22, 1977

[51] Int. Cl.² .............................................. C12C 11/26
[52] U.S. Cl. ....................................... 426/60; 435/255; 435/813; 435/921
[58] Field of Search ..................... 426/60, 62; 195/97, 195/82, 98, 74, 49

[56] References Cited

U.S. PATENT DOCUMENTS

| 479,130 | 7/1892 | Allert | 195/97 |
|---|---|---|---|
| 3,809,776 | 5/1974 | Chao | 426/60 X |
| 3,885,050 | 5/1975 | Ridgway, Jr. et al. | 426/60 |

*Primary Examiner*—David M. Naff
*Attorney, Agent, or Firm*—Gregory E. Croft; Arthur G. Gilkes; William T. McClain

[57] ABSTRACT

The flavor of a yeast product is modified by subjecting a slurry of fresh yeast cells to aeration with an oxygen-containing gas for from less than about 1 to about 120 minutes at a temperature of from about 45 to about 150° C. The resulting yeast product has a bland, slightly sweet, mushroom- and toasted almond-like flavor and a cocoa-like aroma.

9 Claims, No Drawings

METHOD FOR MODIFYING THE FLAVOR OF YEAST

BACKGROUND OF THE INVENTION

1. Field of the Invention

This invention relates to the production of yeast products and, more particularly, to methods of modifying the flavor of yeast products.

2. Description of the Prior Art

Dried yeast products have innumerable uses as functional and nutritional food ingredients. One such product is a dried *Candida utilis* yeast which is grown on a food grade ethanol substrate under oxygen-limiting growth conditions. The fermentor contents are continuously withdrawn and centrifuged to produce an aqueous yeast cell slurry containing about 10-20 weight percent yeast cells. The slurry is then spray dried to yield a powdery product which can be used in numerous food applications. This product generally has a strong yeasty flavor and an aroma that can be affected by growth conditions and after-harvest processing. It is very difficult, from a quality control standpoint, to continuously produce such a dried yeast product which has consistent flavor and color. Some products have a strong yeasty flavor while others have a more mild flavor, even though both products are produced in the same manner. It is desirable to eliminate or reduce the yeasty flavor of the dried product in favor of a consistently more bland tasting product. This is particularly necessary where higher levels of the yeast product are to be used as a food ingredient.

It has now been discovered that a consistantly more bland tasting product having a sweet, mushroom- and almond-type background flavor and a cocoa-like aroma can be produced by a simple post-harvest processing step.

SUMMARY OF THE INVENTION

In one aspect the invention resides in a method for improving the color and flavor of a yeast product derived from a yeast fermentation process which yields a slurry of fresh yeast cells, said method comprising oxygenating the slurry with an oxygen-containing gas having an oxygen partial pressure of at least 0.2 atmospheres for from less than about 1 to about 120 minutes at a temperature of from about 45° to about 150° C. and at a pH of from about 4 to about 7. In carrying out this method it has been found that a slurry of fresh yeast cells is necessary to obtain the desired effects on flavor and color of the yeast. Yeast cells which have been spray dried and reslurried will not benefit from this treatment method. The partial pressure of oxygen used in the treatment should be at least 0.2 atmospheres, which corresponds to the oxygen content in the air. It has been found that the desired reaction rate increases with increasing oxygen partial pressure such that a treatment time of less than 1 minute is necessary to achieve a bland tasting product at 500 psi oxygen partial pressure at about 80° C. In addition, the reaction rate also increases with increasing temperatures. A lower limit of about 45° C. has been selected because the treatment rate is either impractically slow or completely ineffective at lower temperatures. On the other hand, at temperatures above about 100° C. the yeast product may increasingly begin to exhibit a burnt taste at longer treatment times, so that an upper limit of about 150° C. is suggested. A preferred temperature range would be between 80° and 100° C. In this regard it should be mentioned that at the higher temperatures, depending upon the length of treatment time, pasteurization may be effected simultaneously without the need for a separate pasteurization step. Nevertheless, at the lower temperatures it may be necessary to pasteurize the oxygenated slurry. It has also been found that the oxygenation process is more effective at lower pH values. The yeast slurry as it leaves the fermentor generally has a pH of about 4 and must eventually be adjusted to about pH 7 before drying to achieve the most desirable flavor. Therefore, it is preferable that the pH be adjusted to about 7 after the oxygenation treatment to take advantage of the increased reaction rate at the lower pH. The oxygenation treatment itself will gradually raise the pH as the treatment proceeds and generally will raise the pH to about 6. Pasteurization of the slurry directly after leaving the fermentor will also raise the pH to about 6. In such a case the oxygenation can advantageously be carried out at the pH of about 6. Also in this regard, a number of neutralizing agents are suitable such as NaOH, Ca(OH)$_2$, Na$_2$CO$_3$, CaCO$_3$, KOH, K$_2$CO$_3$, and NH$_4$OH. Slight flavor differences result with each different neutralizing agent used, with NaOH and NH$_4$OH being preferred.

More specifically, the invention resides in the above-said method wherein the fresh slurry is oxygenated with an oxygen-containing gas (such as air, enriched air, or pure oxygen) having an oxygen partial pressure of about 0.5 to about 20 atmospheres for from about 1 to about 15 minutes at a temperature of about 80°-100° C., preferably about 90° C. for about 1 minute or so using pure oxygen at 1 to 2 atmospheres pressure.

Although the process of this invention is applicable to any slurry of fresh yeast cells, a preferred yeast is *Candida utilis*.

DESCRIPTION OF SPECIFIC EXAMPLES

The following examples will serve to illustrate various aspects of my invention.

EXAMPLE 1

Yeast cells, *Candida utilis*, were harvested from a continuous culture grown on ethanol under oxygen-limited growth conditions. One liter of cell cream (15% cells by weight) was heated rapidly to 80° C. by a steam coil. The pH of the pasteurized cream was raised from 6.1 to 7.0 by adding 1N NaOH. The cream was maintained at 60° C. and bubbled with oxygen gas under constant stirring for 2 hours. The color changed from light pink to creamy, and the slurry was much less foamy. The treated material was pasteurized and spray dried.

The above experiment was repeated in the same manner with a broken cell slurry, of which the cells had been passed through a Manton-Gaulin homogenizer for 3 times at a pressure of 8000 psi, and at a temperature not over 30° C.

Sensory evaluation was carried out by a tasting panel of seven persons. Each sample was prepared as a 10% suspension in hot water. The results are summarized in Table 1.

TABLE I

| Sample | Flavor |
| --- | --- |
| (a) Control, untreated | Very yeasty, slightly astringent, slightly meaty |
| (b) Whole cell, treated | Very mild, slightly sweet, slightly meaty, slight mushroom-like and toasted almond-like note, slight cocoa-like aroma |
| (c) Broken cell, treated | Same as (b), also slightly salty |

EXAMPLE 2

One liter of cell cream (about 15% cells by weight) was incubated in a two liter fermentor without being previously pasteurized. The reaction was carried out at 30° C. and an oxygen partial pressure of 1 atmosphere. The stirring was maintained at 500 rpm. At the end of 2 hours' incubation, the treated material was pasteurized, neutralized, and spray dried. No significant change in flavor and in color was observed as compared to the control, illustrating the fact that the oxygenation treatment is ineffective at a temperature of 30° C.

EXAMPLE 3

Five hundred ml. of a pasteurized and neutralized cell slurry (15% cells by weight) was treated with pure oxygen gas in a closed system of a two liter fermentor, wherein the internal gas was recirculated through the slurry by a pump. The reaction was carried out at 60° C. and a stirring rate of 900 rpm. The oxygen partial pressure was varied. The samples of slurry were withdrawn periodically for flavor tasting. As indicated in Table II, the rate of flavor change is dependent upon the partial pressure of oxygen. Rancidity developed when the material was over-oxygenated.

TABLE II

| | Oxygen Partial Pressure, (Atm.) | |
| --- | --- | --- |
| Time, Min. | 0.4 | 1.2 |
| 0 | Very yeasty | Very yeasty |
| 10 | Yeasty | Mild |
| 20 | Yeasty | Mild, slightly rancid |
| 30 | Slightly yeasty | More rancid |
| 40 | Mild | — |
| 50 | Mild | — |
| 60 | Mild, slightly rancid | — |

EXAMPLE 4

One liter of a pasteurized and neutralized cell slurry (15% cells by weight) was treated with pure oxygen in a closed system of a two liter fermentor. The reaction was carried out at an oxygen partial pressure of 1 atmosphere and a stirring rate of 500 rpm. Internal gas was not recirculated. Temperature was varied between 30° C. and 60° C. Samples of the slurry was withdrawn periodically for flavor tasting and color measurement. The red color component was measured by a Hunterlab Color Difference Meter Model D25. The results are summarized in Table III, which shows that the change of both flavor and color is temperature-dependent.

TABLE III

| Time, Min. | Red Color (Hunter's Scale) | | Flavor | |
| --- | --- | --- | --- | --- |
| | 30° C. | 60° C. | 30° C. | 60° C. |
| 0 | 4.0 | 4.0 | Very yeasty | Very yeasty |
| 5 | 4.0 | 2.3 | Very yeasty | Mild |
| 10 | 3.8 | 1.7 | Yeasty | Mild |
| 15 | 3.5 | 1.0 | Slightly yeasty | Mild, slightly rancid |
| 30 | 2.9 | 0.3 | Mild | Mild, rancid |

EXAMPLE 5

One liter each of a pasteurized cell slurry (15% cells by weight) was adjusted to pH 6.1, 6.8, or 7.8 by using 1N NaOH as a neutralizing agent. The materials were treated with oxygen gas at 60° C. in a fermentor system as described in Example 4. A sample of the slurry was withdrawn periodically and neutralized to pH 7.0 before it was tested. As summarized in Table IV and FIG. II, the results indicate that the rate of change in color (red color, Hunter's scale) and in flavor is pH-dependent. Oxygenation is preferably carried out at the lower pH values.

TABLE IV

| Time, Min. | Flavor/Color | | |
| --- | --- | --- | --- |
| | pH 6.1 | pH 6.8 | pH 7.8 |
| 0 | Very yeasty/4.0* | Very yeasty/4.0 | Very yeasty/4.0 |
| 5 | Yeasty/1.8* | Mild/2.3 | Yeasty/3.5 |
| 10 | Mild/0.8* | Mild/1.7 | Slightly yeasty/2.8 |
| 15 | Mild/0.6* | Mild, slightly rancid/1.0 | Mild/2.3 |
| 30 | Mild, slightly rancid/0.1* | Mild, rancid/0.3 | Mild, slightly rancid/0.3 |

*Color readings adjusted to account for the starting material having an initial color of 3.4. The adjustment was made to provide a proper comparison to the other samples which had a starting color of 4.0.

EXAMPLE 6

A batch of pasteurized cell slurry (15% cells by weight), which was unusually light in color and very mild in flavor, was treated with oxygen at 60° C. by the same method as described in Example 4. As shown by the results in Table V, the slurry samples treated at various periods of time did not give any significant difference in the flavor since the starting material had such a mild flavor. Rancidity was not noticed in the samples treated up to 30 minutes, and the red color component was completely removed.

TABLE V

| Time, Min. | Red Color (Hunter's Scale) | Flavor |
| --- | --- | --- |
| 0 | 0.7 | Mild |
| 5 | 0.5 | Mild |
| 10 | 0.3 | Mild |
| 15 | −0.1 | Mild |
| 30 | −1.1 | Mild |

It will be apparent to those skilled in the art that many variations from these examples, shown for purposes of illustration, can be made without departing from the scope of this invention.

We claim:

1. In a yeast fermentation process resulting in about a 10 to about 20 weight percent aqueous slurry of fresh yeast cells, a method for improving the color and flavor of the yeast product comprising oxygenating the slurry with an oxygen-containing gas having an oxygen partial pressure of from about 0.5 to about 20 atmospheres for from about 1 to about 15 minutes at a temperature of from about 80° to about 100° C. and at a pH of from about 4 to about 7.

2. The process of claim 1 wherein the pH of the oxygenated slurry is adjusted to from about 6.8 to about 7.0 and the pH adjusted slurry is spray dried.

3. The proces of claim 1 wherein the oxygen-containing gas has a partial pressure of from about 0.5 to about 2.0 atmospheres.

4. The process of claim 1 wherein the yeast is *Candida utilis*.

5. In a continuous fermentation process wherein *Candida utilis* yeast cells are grown on an ethanol substrate under conditions of oxygen-limited growth and are harvested to give an aquous slurry of fresh yeast cells having a concentration of from about 10 to about 20 weight percent, a method for improving the flavor and color of the ultimate yeast product comprising oxygenating the aqueous slurry with an oxygen-containing gas having an oxygen partial pressure of about 1 atmosphere at a temperature of about 90° C. for about 5-10 minutes at a pH of about 6.

6. The method of claim 5 wherein the oxygenated slurry is adjusted to a pH of about 6.8–7.0 and spray dried.

7. The method of claim 6 wherein the pH is adjusted by the addition of a neutralizing agent selected from the group consisting of NaOH, $Na_2CO_3$, $Ca(OH)_2$, $CaCO_3$, KOH, $K_2CO_3$, and $NH_4OH$.

8. The method of claim 6 wherein the neutralizing agent is NaOH.

9. The method of claim 6 wherein the neutralizing agent is $NH_4OH$.